United States Patent [19]

Lommen et al.

[11] Patent Number: 4,985,036

[45] Date of Patent: Jan. 15, 1991

[54] ARTIFICIAL SKIN

[75] Inventors: Etienne J. C. M. P. Lommen; Charles R. H. Wildevuur; Wouter L. J. Hinrigs, all of Groningen, Netherlands

[73] Assignee: Koninklijke Utermohlin N.V., Utrecht, Netherlands

[21] Appl. No.: 376,604

[22] Filed: Jul. 7, 1989

[30] Foreign Application Priority Data

Jul. 8, 1988 [NL] Netherlands .................. 8801741

[51] Int. Cl.$^5$ .............................................. A61F 2/10
[52] U.S. Cl. ...................................... 623/15; 128/156; 523/113; 523/114
[58] Field of Search ............... 623/15, 66, 1; 210/488, 210/490; 128/156, 155; 523/111, 113, 114

[56] References Cited

U.S. PATENT DOCUMENTS

| | | | |
|---|---|---|---|
| 4,642,118 | 2/1987 | Kuroyanagi et al. | 623/15 |
| 4,725,273 | 2/1988 | Kira | 623/1 |
| 4,813,966 | 3/1989 | Gilding et al. | 623/66 |
| 4,822,352 | 4/1989 | Joh et al. | 623/1 |
| 4,947,840 | 8/1990 | Yannas et al. | 128/156 |

FOREIGN PATENT DOCUMENTS

| | | |
|---|---|---|
| 0117438 | 9/1984 | European Pat. Off. |
| 0265906 | 5/1988 | European Pat. Off. |
| 2577133 | 8/1986 | France |
| 2093703 | 9/1982 | United Kingdom |

Primary Examiner—Alan W. Cannon
Attorney, Agent, or Firm—Young & Thompson

[57] ABSTRACT

A material which transmits wound moisture, made up of an upper layer of an elastomer having a thickness of 0.01–0.2 mm which is provided with pores having a diameter not exceeding 0.7 μm and a pore density of 1–75% of the surface, and a lower layer of an elastomer having a thickness of 0.05–1 mm which is provided with macropores having a diameter of 50–200 μm, at least some of the walls of said macropores being provided with micropores having a diameter of 0.1–0.25 μm, is provided. The material of the invention meets a number of conditions making it suitable for the use of artificial skin.

10 Claims, 8 Drawing Sheets

ARTIFICIAL SKIN

The invention relates to an artificial covering which can be used externally as artificial skin for skin lesions such as burns, grazes and the like and also internally as artificial mucous membranes for repairing defects in the respiratory tract, digestive system or for the urinary tracts in the form of an artifical trachea, artificial intestine or artificial ureter/urethra. For the time being the emphasis in the use of the artificial covering according to the invention is on the external use.

As is known, the human skin forms a protective barrier against external influences. However, if large sections of the skin are damaged, as in the case of burns, this protective function is lost and human life is threatened by two complications, viz. drying out as a result of loss of moisture and infection by invading bacteria. One solution to this problem may be sought in skin transplantation (autograft). This implies the transplanting of skin from one part of the body to the other part. The paradox of this method is that, on the one hand, a defective section of skin is covered while, on the other, a new lesion is created. Use may also be made of prepared human or animal skin, but this is associated with a wide variety of problems such as those relating to antigenicity, bacterial infection, limited quantities and relatively high costs.

With the above problems in mind, research has been made for an artificial skin which is able to fulfil two very important functions, viz. the reduction of the moisture loss as a result of evaporation from the wound surface and the prevention of infection. As will be discussed in more detail below, various types of plastic film are already known as artificial skin. Many have the disadvantage, however, that wound moisture accumulates underneath, as a result of which the artificial skin becomes detached. The problems relating to the known artificial skins may, however, be ascribed to two seemingly opposing requirements which an artificial skin should fulfil:

(a) on the one hand, the artificial skin should be "impervious" in order to keep bacteria outside the body and to prevent loss of water vapour, and (b) on the other hand, the artificial skin should be sufficiently "open" to make an optimum passage of wound moisture possible.

Macromol. Chem. Rapid Communications 4, 675–680 (1983) discloses, for example, an artificial skin which is made up of two membranes bonded to each other. The lower layer which is to be applied to the bed of the wound is composed of a biodegradable poly(lactic acid)/polyurethane blend and contains pores having a diameter of 40–200 $\mu$m to promote tissue growth. This lower layer is gradually hydrolyzed after application and is replaced by newly formed tissue. The upper layer, on the other hand, is composed of nonbiodegradable polyurethane and contains pores having a diameter of 0.5–1.0 $\mu$m. Said upper layer, which is intended to protect the wound against a bacterial invasion and has to ensure an adequate transport of water vapour, is reported to be removed after the wound in the skin has healed. However, in addition to the complexity of the production method reported therein for such an artificial skin, it also has the disadvantage that the biodegradable lower layer, which, according to the example contains 80% by weight of polyurethane, will yield polyurethane fragments which are injurious to the body, after hydrolysis and which will only be excreted from the body after a long time. Furthermore, the adhesion of this known artificial skin to the bed of the wound leaves something to be desired, with the result that the risk of bacterial infection is considered to be undesirably high.

In Burns (1985) 11, 274–280, a description is given of an artificial skin which is based on a polyurethane membrane and which is marketed under the name "Omiderm". More particularly, "Omiderm" is made up of a polyurethane film to which hydrophilic monomers such as hydroxymethacrylate and/or acrylamide are grafted. Such a membrane, which has a thickness of 40 $\mu$m, is hydrophilic, elastic only in the moist state, transparent and capable of absorbing its own weight of water. In the dry state, however, the film is fairly inelastic and has the tendency to dry out after application which gives rise to the formation of wrinkles and some contraction. Despite the high permeability to water vapour of approx. 200 g/m$^2$.h, the evaporation may still be inadequate in the case of burns during the exudative phase with the result that undesirable blister formation occurs; see Burns (1986), 12, 587–591, in particular Table I. If blister formation occurs, the artificial skin should be replaced, in which case the risk of bacterial infection then occurs. Another disadvantage of "Omiderm" is that the abovementioned high permeability to water vapour does not adequately limit the evaporation from the patient to the air in the case of other types of skin wounds, as a result of which undesirable loss of moisture occurs. Furthermore, "Omiderm" is unsuitable for use on "full-thickness" burns since the adhesion of the artificial skin leaves something to be desired and is accompanied as a result by a high level of bacterial infection.

Another commercially available artificial skin is Biobrane (Burns 7, (1979), 123–130). More particularly, this Biobrane artificial skin is composed of a flexible nylon fabric and a protective silicone-rubber membrane. Both layers are covered with a layer of hydrophilic collagen peptides. The upper silicone-rubber layer is mechanically punctured in a regular manner in order to make a drainage of wound moisture possible. This known artificial skin also has, as will be demonstrated below, a wide variety of disadvantages such as inadequate protection against a bacterial infection.

On the basis of an investigation by the Applicant, an artificial skin has now been found which does not have the disadvantages associated with the known artificial skins. More particularly, the artificial skin according to the invention has the following desirable properties:

(1) the artificial skin immediately and readily adheres firmly to the surface of the wound and remains permanently stuck until the wound healing process is complete.

(2) the artificial skin can be applied pliantly over the surface of the wound, air bubbles being displaced through the material;

(3) the artificial skin immediately alleviates the pain occurring with a wound;

(4) the artificial skin has blood-stemming properties;

(5) the artificial skin reduces the production of wound moisture;

(6) the artificial skin makes an ample passage of wound moisture possible and as a result prevents blister formation under the material. Combination with an overlying material which absorbs wound moisture makes it possible to increase the passage of wound moisture through the artificial skin considerably, for example from 1,800 g/m².h to 4,400 g/m².h (measured at a hydrostatic pressure of 2 cm H₂O) (see FIG. 5);

(7) the artificial skin prevents the invasion of bacteria but makes possible a passage of antimicrobial agents which have been applied;

(8) the artificial skin promotes the bacterial-killing properties of the surface of the wound and may even be applied to contaminated wounds;

(9) the artificial skin is transparent after application to the surface of the wound, with the result that the course of the healing process can be followed in a simple manner;

(10) the artificial skin reduces the contraction occurring in the case of wounds;

(11) the artificial skin boosts the speed of repair of the epidermis and the quality of the healed epidermis;

(12) the artificial skin does not produce any allergic reactions;

(13) the artificial skin is relatively easy to use and can be stored for a long time; and (14) the artificial skin is easy to sterilize (for example by gas sterilization or gamma-ray sterilization).

The artificial skin according to the invention, which satisfies the abovementioned points, is made up of:

(a) an upper layer of an elastomer having a thickness of 0.01–0.2 mm which is provided with pores having a diameter not exceeding 0.7 μm and a pore density of 1–75% of the surface, and (b) a lower layer of an elastomer having a thickness of 0.05–1 mm which is provided with macropores having a diameter of 50–200 μm, at least some of the walls of the said macropores being provided with micropores having a diameter of 0.1–0.25 μm, the micropores in the walls of the lower layer advantageously extending to the micropores in the upper layer.

The micropores in the walls of the macropores of the lower layer preferably have a diameter of 0.1–5 μm. The vacant volume:total volume ratio of the lower layer is preferably in the range of 0.05–0.95.

It is pointed out that the PCT Patent Application WO No. 86/2843 describes a method of producing an artificial skin in which mention is made of a two-layer membrane composed of an uppermost protective layer having a porosity in the range of 0.4–0.9 μm and a lower layer having a porosity in the range of 100–150 μm. This composite membrane offers a satisfactory protection against the invasion of bacteria and ensures the desired water and gas transport to and from the wound. It is stated that the use of said membrane facilitates the healing process of noninfected wounds. From tests carried out by the Applicant it has emerged, however, that the method of said PCT patent application does not yield the artificial skin according to the invention; in particular, the micropores are absent in the walls of the macropores in the lower layer.

The artificial skin according to the invention is advantageously made up of thermoplastics having elastomeric properties such as block polyurethanes, polyether esters and also silicone rubbers which have a desired elasticity, strength and biocompatibility. More in particular are block polyurethanes, polyester urethanes and polyether urethanes which are, for example, based on poly(tetramethylene adipate), poly(ethylene glycol adipate), poly(tetramethylene oxide), poly(diethylene glycol adipate), 3,4'- and 4,4'-diphenylmethane diisocyanate, toluene diisocyanate, hexamethylene diisocyanate with, for example, 1,4-butanediol and ethylene diamine as a chain extender.

The abovementioned block polyurethanes are known from the prior art. A wide variety of examples of block polyurethanes is mentioned in the book entitled "Polyurethanes in medicine", chapter 5, "Biomedical polyurethanes", pages 57–71. One of the suitable polyurethanes is the commercial product "Biomer", which is a copolymer of polytetramethylene oxide and 4,4'-diphenylmethane diisocyanate with a mixture of diamines, mainly ethylene diamine as a chain extender. Other commercially obtainable polyetherurethanes which are suitable as a material for the artificial skin according to the invention which may be mentioned are, for example, "Pellethane 2363 75A" and "Pellethane 2363 80A" [Upjohn Co.] which is essentially made up of poly(tetramethylene oxide) and 4,4'-diphenylmethane diisocyanate with 1,4-butanediol as chain extender, and also "Cardiothane" [Contron, Cardiovascular Inc., U.S.A.] and "Tecoflex" [Thermo Electron Corp., U.S.A.]. Furthermore, the product "Hytrel" [DuPont de Nemours, U.S.A.] may be mentioned as polyether ester.

The artificial skin according to the invention, which advantageously has a thickness of 0.06–0.2 mm, has the advantage that, once it has been applied, it no longer needs to be removed in order to remove the accumulated exudates at regular times, as in the case of many known artificial skins. This procedure of removing and replacing the artificial skin in fact implies an appreciable risk of bacterial infection which therefore frequently occurs.

A bacterial infection cannot normally take place via the artificial skin according to the invention since the micropores in the upper layer have a size not exceeding 0.7 μm. This maximum pore size is related to the impossibility of *Pseudomonas aeruginosa*, which is regarded as most frequently occurring and a notorious pathogen affecting skin lesions, passing through the upper layer to reach the skin lesion. In order to be able to act as a complete barrier to all bacteria, the upper layer should be provided with micropores having a size of 0.22–0.44 μm. However, in certain cases, with such a pore size range, the pore density of the upper layer has to be adjusted in order to be able to maintain the drainage capacity thereof for wound moisture.

The application of the artificial skin according to the invention will make it possible to considerably limit the moisture loss due to evaporation which, in patients having serious burns, may well amount to 7 liters per day, for example to a value of approximately 85%. This restriction in moisture loss will also considerably reduce the requirement for additional energy necessary for the evaporation, which would benefit the disturbed metabolic energy balance of the seriously ill patient.

In view of the pore density of the microporous upper layer of 1–75%, preferably 25–40% of the surface, the drainage capacity of this layer is very large and normally adequate for the quantity of exudate originating from skin lesions. The use of absorbent material such as cotton gauze on the artificial skin yields, in addition, an increase in the drainage capacity by a factor of 2 to 3.

In relation to the lower layer of the artificial skin according to the invention, it is emphasized that the construction thereof is made up in such a way that an immediate and good adhesion to the bed of the wound is achieved. At the same time the micropores in the walls play an important role: they exert a strong capillary suction force which causes immediate adherence to the wet wound bed and also promotes the transport of exudate, in particular, if many of said micropores form a "continuum" with the pores in the upper layer. This is in contrast to other microporous artificial skins in which the micropores do not form a "continuum" but are present as sealed air-containing cavities. In a later stage of the healing process, the fibrin formed largely ensures the adhesion between the artificial skin and the bed of the wound. The degree of this adhesion is in this case dependent on the contact properties provided by the lower layer of the artificial skin for the fibrin. For this purpose, the under layer structure according to the invention makes the desired contribution. These adhesion properties of fibrin are clearly evident from FIGS. 6 and 7; the appreciable decrease in adhesion in heparinized groups of animals can be ascribed to the effect that heparin counteracts the formation of fibrin by blocking the conversion of prothrombin into thrombin.

Advantageously, the lower layer has a thickness of 0.1–0.7 mm and the vacant volume to total volume ratio has a value of 0.7–0.9.

Figure 1:
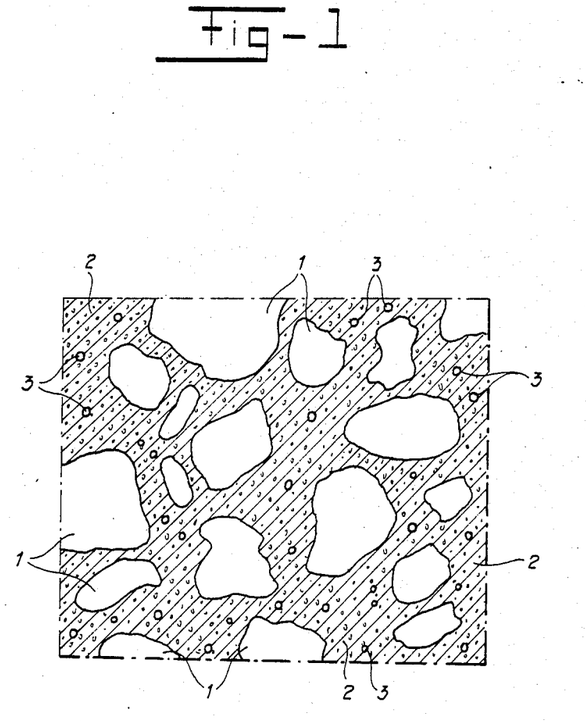
FIG. 1: Diagrammatic side view of the a lower layer (2) artificial skin according to the invention which is made up of an upper layer provided with micropores and the pictures lower layer containing a macroporous fibrillated sponge structure.

The lower layer of the artificial skin according to the invention is shown diagrammatically in FIG. 1 in which (1) represents the macropores, (2) represents the partitions walls of said macropores and (3) represents micropores interspersed with the macropores throughout the thickness of the layer.

In the artificial skin according to the invention, the upper and the lower layers may form one entity, this referring to a gradual transition of the parameters of lower and upper layers. Such an artificial skin may, for example, be produced by techniques which are used to make membranes.

The artificial skin according to the invention can be produced in a wide variety of ways. One of the methods used is based on the principle of immersion precipitation. In this process, a polymer solution is brought into contact with a nonsolvent. As a result, an outflow of solvent and an inflow of nonsolvent takes place, which results in a phase separation in which polymer-rich and low-polymer regions are produced. The polymer-rich regions ultimately form together the polymer matrix, while the low-polymer regions start to form the (micro) pores. The choice of the solvent, the nonsolvent, the polymer concentration, the layer thickness of the polymer solution applied and the temperature determine the pore size or pore size distribution and the porosity of the product.

An extraporosity-inducing factor can be introduced by adding salt particles to the polymer solution. During the precipitation of this suspension by bringing it into contact with a nonsolvent, the salt particles are enclosed by a matrix of the polymer. (Micro) pores are produced in this matrix by the process of phase separation described above. In addition to the factors mentioned previously, therefore, the presence of the salt particles will also influence the pore size or pore size distribution and the porosity. Macropores are produced by subsequently removing the salt particles by means of extraction.

The artificial skin according to the invention may, for example, be manufactured as follows.

(A) Production of the lower layer

A solution of, for example, the product "Biomer" in N,N-dimethylacetamide with sodium citrate particles having a size of 60–100 μm added to it is spread out over a glass plate which is provided with an adjustable skimming device. Using said adjustable skimming device, a layer of the suspension of the salt particles in the polymer solution can be obtained which has an adjusted thickness of, for example, 350 μm. This film is coagulated in a mixture of ethanol/distilled water for a few minutes and dried in air.

(B) Deposition of the upper layer

After the lower layer has largely been dried, a second "Biomer" solution is deposited on the lower layer. The two layers are immersed in ethanol for 10 minutes, which results in the coagulation of the upper layer of, for example, 20 μm. The two-layer product is then placed in a water bath at 20° C. in order to extract the salt crystals and also solvent residues.

In this procedure, the amount, size and size distribution of the sodium citrate crystals, the temperature, the concentration of the polymer solution and the composition of the coagulation agent govern the size obtained of the macropores and the residual structure of the lower layer.

As stated, the lower layer may be produced from biodegradable material. However, in view of the disadvantages mentioned above, it appears undesirable to modify the properties of the material in this way if this results, on use, in fragments which are injurious to the body.

To achieve a better insight in relation to the artificial skin according to the invention, there follows below a discussion of:

(a) the upper layer separately;
(b) the lower layer separately; and
(c) the combination of upper layer and lower layer.

Re (a). The function of the microporous upper layer

From an in vitro investigation, the following requirements imposed on an upper layer of artificial skin according to the invention were investigated in more detail: the prevention of a bacterial invasion and an excessive loss of water vapour, and also the provision of an adequate liquid passage and a rapid penetration of topically applied antibiotics. The results were compared with the commercial product Biobrane.

(1) Bacteriology

Circular disks (diameter 1.5 cm) sterilized with ethylene oxide gas of the upper layer according to the invention and of "Biobrane" were deposited on an cetrimideagar plate. A suspension of 0.2 ml of a rapidly dividing culture of *Pseudomonas aeruginosa* was pipetted into the centre of the material. The agar plates were incubated for 24 hours at 37° C. The agar under each disk was removed with a knife and separately dissolved in 10 ml of sterile water by shaking on a Vortex. Uricult dipslides were immersed in each suspension and kept there for 24 hours at 37° C. The dipslides were investigated for bacterial growth under retroreflected lihgt. It is possible to detect even very small colonies using this method. The number of *Ps. aeruginosa* colonies was counted and compared with the growth values on a Uricult reference chart, the number of bacteria per liter of agar suspension also being determined. Values of less than $5 \times 10^7$ bact./liter were regarded as negative in view of the small errors due to atmospheric contamination.

(2) Penetration of antibiotics

Agar plates were inoculated with a standardized *Ps. aeruginosa* suspension. Sterile disks (diameter: 1.5 cm) of the upper layer of the artificial skin according to the invention and of "Biobrane" were placed on the inoculated agar. As a control, one group of inoculated agar plates was left uncovered while the other group was covered with impermeable, sterile, stainless-steel disks. 1 gram of silver sulfadiazine cream (the product "Flammazine") was spread evenly over the centre of the disk (diameter: 1 cm) so that the outside edge remained uncovered. Two groups of agar plates were incubated for 6 hours and 24 hours at 37° C. The agar zones incubated for bacteria growth were punched out (diameter: 1 cm) and suspended in 10 ml of sterile water. The procedure for counting the bacteria was carried out in the manner described above.

(3) Water vapour transport

The water vapour transport was determined using a "ServoMed Evaporimeter Ep I", an apparatus obtainable commercially which was originally developed for determining the water loss from serious burns (Evaporimeter Users Manual by ServoMed AB Brochure No. 71.401 Ep I). Samples of the upper layer of the artificial skin according to the invention and Biobrane were used to seal a flask which contained a continuously heated and stirred physiological salt solution at 37° C. The measuring point of the Evaporimeter was sited within a distance of 1 cm from the materials and the water vapour transport was determined for each sample.

(4) Wound drainage

The wound drainage was determined quantitatively by allowing a column containing serum to run through the membranes. A hollow glass tube was closed at the top with a rubber stopper and then an artificial skin was fitted over the opening (diameter 2 cm) at the bottom. In doing this, it was necessary not to stretch the elastomeric artificial skin too far since this affects the pore size and the drainage properties. When the rubber stopper at the top was removed, the serum began to pass through the membranes. 20 membranes of each material were always used in the tests. The specific drainage resistance was calculated as the quotient of the hydrostatic pressure P for the membrane and the resulting drainage flow Q divided by the membrane surface area A. The formula is as follows:

$$R\text{-drainage} = P/Q/A = P \times A/Q,$$

where P is determined by the product of the height of the column and the density of the liquid. The qualitative effect of an additional wound drainage was evaluated by using absorbent cotton gauze placed against the membrane.

Re (b). Structure and adhesive properties of the lower layer (1) Materials:

A number of types of polyurethane lower layers were produced using the precipitation techniques below. Various techniques are used to get to a type 4 lower layer from a smooth base layer (type 1) structure via a layer having 50-200 μm macropores (types 2 and 3). The type 4 structure contains fibrillated interstices which produce an open sponge-like structure, globular polymer particles and a microporous structure which yields capillary channels (see FIG. 1). Type 5 is the combination of upper layer (type 6) with lower layer (type 4), the micropores in the two layers merging into each other and forming a continuum. As a control, use was made of a microporous upper layer (type 6), an autograft (type 7) and Biobrane (type 8).

(2) Tensiometry

Figure 2:
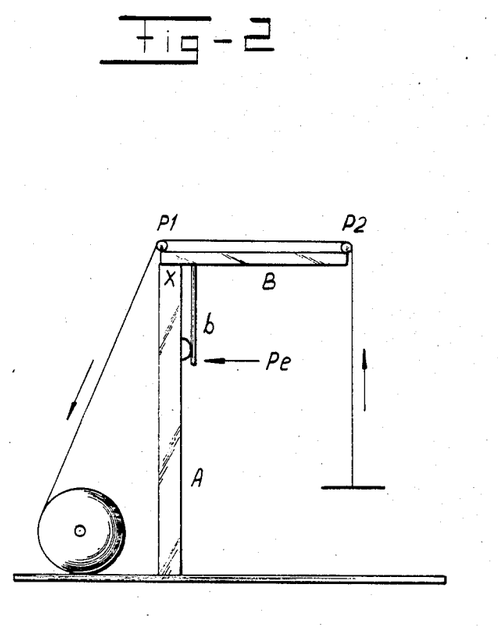
FIG. 2: Diagrammatic side view of the tensiometer.

To provide a roliable quantitative method for determining the degree of immediate adhesion of the artificial skin to the bed of the wound, the Applicant has developed a tensiometer. Its characteristics are shown diagrammatically in FIG. 2. The abovementioned tensiometer comprises a vertical bar A and a movable arm B which is mounted at point X by means of a hinge. A small side arm B of the movable arm rests against a weight transmitting device.

A variable speed electric motor provides a variable traction on a nonelastic wire which runs over two pulley rollers P1 and P2. By moving a weight vertically at a constant speed, a constant force is exerted on the pressure-registering electrode Pe between the two movable arms. The pressure-registering electrode is connected to an amplifier which transmits the amplified signal to a pen recorder. The tensiometer is calibrated by means of known weights. This tensiometer has been specially designed for a vertical movement of artificial skin from the bed of a wound so that the effect of shear forces is minimal. In doing this, the artificial skin is bonded to the vertically movable rod by means of a cyanoacrylate glue (see FIG. 2).

CALCULATION;

The results are shown as force/unit surface=N (speed of electric motor × width of prosthesis). Since the speed of the electric motor was set at 1 cm/sec in all the measurements and the width of the skin prostheses was 2 cm, the formula for an applied force of x newtons becomes as follows:

$$F/A = x.N(1 \text{ cm} \times 2 \text{ cm}) = 0.5. \times .N/\text{cm}^2.$$

(3) Wound drainage

Wound drainage was evaluated qualitatively by wound observation. In this connection, special attention was paid to the formation of blisters under the membranes.

(4) Evaporimetry

The daily measurement of water vapour loss was determined by tracing the measuring point of the evaporimeter within a distance of 1 cm of the material. The measurements were carried out in a draught-free chamber at 27° C.

Re (c). Properties of the combined upper and lower layers of the artificial skin according to the invention The properties studied in the case of the upper layer and lower layer respectively were also determined for the artificial skin according to the invention as such. The data in this connection are reported in the examples below. More particularly, it may be stated that the artificial skin according to the invention produces an appreciable reduction in the water vapour loss (EWL). When used in vivo, the EWL decreased, which is probably to be ascribed to a decrease in the wound exudate production. Furthermore, a further decrease in the EWL with time was observed, with the result that this value became virtually identical to the EWL of normal skin after a time period of 7 to 8 days. This self-regulating normalization of the EWL may be ascribed to the stasis and drying up of serum in the micropores which are no longer draining actively. Said micropores are in fact sealed by crust formation, as a result of which the artificial skin becomes increasingly less permeable to moisture.

In relation to Biobrane it is pointed that it had a large initial EWL reduction but, owing to the limited drainage capacity (too few openings), gave rise to the formation of blisters. These serum-filled blisters under the Biobrane contain an ideal growth medium for microorganisms which were able to invade simply via the openings the upper layer of the Biobrane. This had the consequence that pus formation occurred, and, indeed to such an extent that the Biobrane artificial skin was generally shed from the bed of the wound well within the healing time. Such a phenomenon did not occur in a single case with the artificial skin according to the invention.

It is furthermore emphasized that it has been found both experimentally and clinically that an artificial skin which adheres well to the wound exerts a bactericidal activity on the wound flora. Said bactericidal activity of a well-adhering artificial skin has been clearly demonstrated in tests in which the artificial skin according to the invention prevented an infection of the wound which had been deliberately contaminated with *Pseudomonas aeruginosa*. Said bactericidal activity is ascribed to a number of factors. A well-adhering membrane such as the artificial skin according to the invention prevents dead spaces, which are a source of bacterial proliferation, while blister formation with an accumulation of lysed leucocytes limits phagocytosis. Covering the wound increases the local degree of acidity and temperature, and this is known to promote said phagocytosis. The total action is thus based on stimulating the physiological anti-bacterial defence mechanism of the host. A treatment of the infected wound by using a topically applied antimicrobial agent on the artificial skin according to the invention proved more effective than in the case of Biobrane.

In summary, it may be stated that the artificial skin according to the invention effectively reduces the EWL and, at the same time, makes an effective wound drainage possible in vivo while preventing blister formation. The artificial skin according to the invention furthermore has a bactericidal activity on wound surfaces which were deliberately infected. In addition, a rapid penetration of topically applied antimicrobial agents makes possible an effective treatment of contaminated wounds.

The invention is explained in more detail with reference to the examples below; these should not, however, be interpreted as restrictive.

EXAMPLE I

Production of an artificial skin according to the invention having a nonbiodegradable lower layer.

(A) Base layer

A solution was prepared of the commercial product "Biomer" (8.6 g/100 ml) in N,N-dimethylacetamide with sodium citrate particles having a size of 63-106 $\mu$m (80 g/100 ml degassed at a temperature of 50° C.) added to it. A glass plate having dimensions of 40×40 cm was rinsed with ethanol and dried in air. Then the suspension of the salt particles in the Biomer solution was spread over the glass plate and adjusted with an adjustable skimming device in a manner such that a layer of the suspension of the salt particles in the polymer solution was obtained which had a thickness of 350 $\mu$m. This layer was coagulated with a mixture of ethanol/- distilled water (6:1 v/v; 20° C.; degassed) for 2 min and dried in air to produce a virtually dry product.

(B) Upper layer

At this stage of the production, a second layer of a Biomer solution having a thickness of approx. 250 $\mu$m was matched with the base layer already obtained. In this case, a Biomer solution of 11.5 g/100 ml in N,N-dimethylacetamide was used. The two layers were immersed in ethanol (100%) for 10 min, which resulted in the coagulation of an upper layer having a thickness of 20 $\mu$m. The product comprising two layers was finally immersed in a water bath at room temperature in order to extract the salt crystals and also the solvent residues. Then the product obtained was dried in air.

An artificial skin was obtained which had a microporous upper layer having 0.4-0.7 $\mu$m pores and a thickness of 20 $\mu$m and a macroporous base layer having 50-100 $\mu$m macropores, a thickness of 100 $\mu$m, and also having a fibrillated sponge structure containing globular precipitation, which structure was provided, in addition, with micropores having a diameter not exceeding approximately 5 $\mu$m. The vacant volume:total volume ratio of the lower layer was approximately 0.85.

EXAMPLE II

Production of an artificial skin according to the invention having a biodegradable lower layer.

The procedure is as described in Example I, but with the difference that the biodegradable lower layer was produced using a mixture of Biomer/poly($\epsilon$-caprolactone) 90/10 (w/w) (molecular weight of poly($\epsilon$-caprolactone)=70,000).

EXAMPLE III

Properties of the microporous upper layer according to the invention as such, manufactured according to Example I using a glass plate.

The tests carried out in vitro which have been described above yielded the following results:

(1) Bacteriology (n=30)

The impermeable stainless-steel control disks prevented a bacterial penetration, as did the upper layers according to the invention, with one exception. The Biobrane used as comparison material revealed a bacterial penetration in 11 of the 30 cases.

(2) Water vapour transport (see FIG. 4) (n=10)

Figure 4:
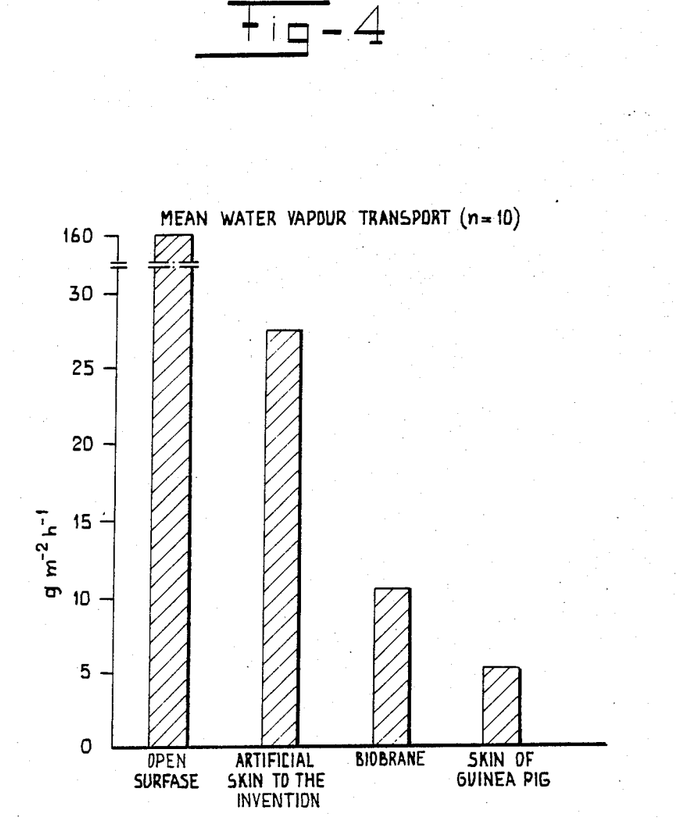
FIG. 4: Graphical representation of the water vapour transport for, in sequence, an open surface, the upper layer of the artificial skin according to the invention, Biobrane and for the skin of a guinea pig (n=10).

The surface above the salt solution exhibited a mean water vapour loss of 160 g.m$^{-2}$.h$^{-1}$. Biobrane artificial skin limited the water vapour transport to 10.5 g.m$^{-2}$.h$^{-1}$, while the microporous polyurethane upper layer according to the invention revealed a water vapour transport of 28.4 g.m$^{-2}$.h$^{-1}$.

(3) Wound drainage (see FIG. 5) (n=30)

Figure 5:
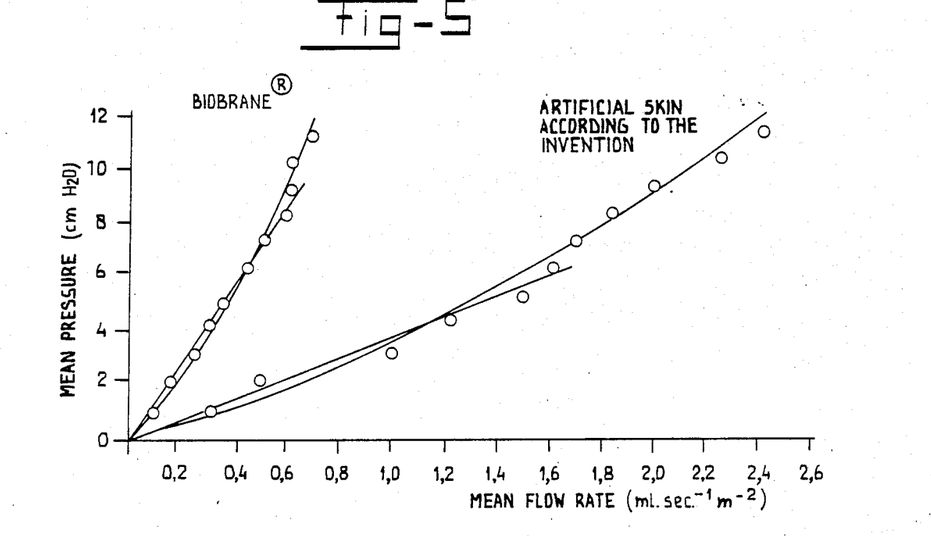
FIG. 5: Graphical representation of the results of the in vitro drainage test with Biobrane and the upper layer of the artificial skin according to the invention.

The mean specific drainage resistance (STR) was approximately three times as high for Biobrane as for the upper layer according to the invention, viz. 3.54 and 1.08 cm H$_2$O.sec/ml.cm. At the same time, the polyurethane upper layers according to the invention exhibited reproducible drainage values, a property which Biobrane did not satisfy.

An important fact was that by gently pressing cotton gauzes against the materials, it was possible to increase the serum drainage through the upper layer according to the invention by a factor of 2 to 3, while it was only 1.3 for Biobrane.

(4) Penetration of antibiotics (see FIG. 3) (n=15)

Figure 3:
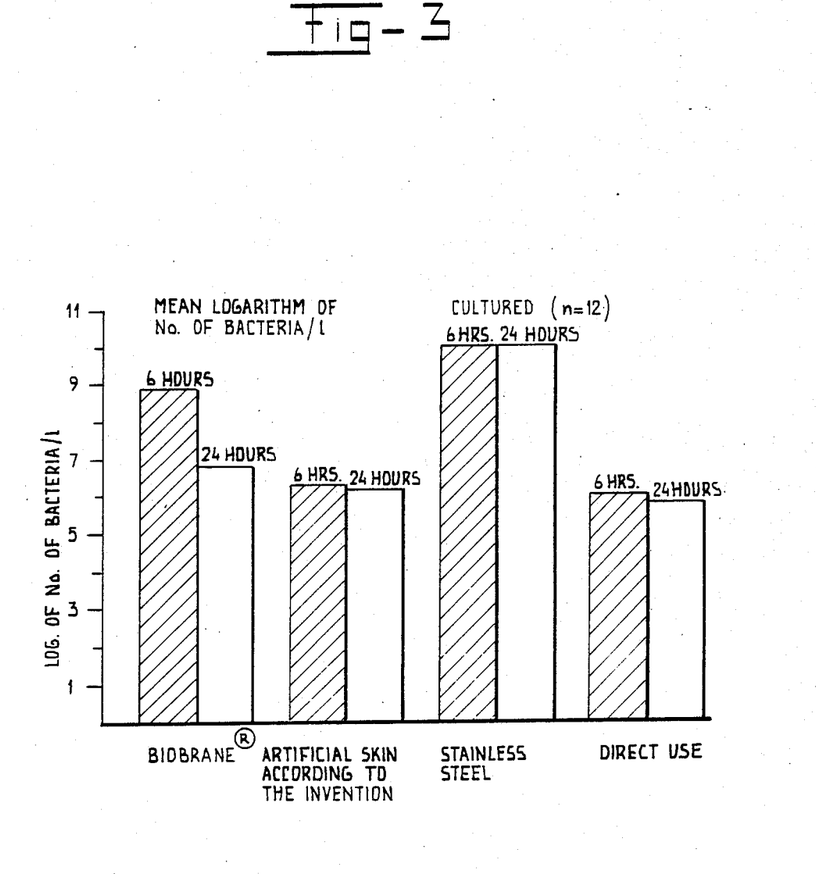
FIG. 3: Graphical representation of the results of the in vitro silver sulfadiazine penetration test for, in sequence, Biobrane, the upper layer of the artificial skin according to the invention, stainless steel and direct use (n=12).

The highest bacterial value was found for the control group containing the inoculated agar plates which were covered with the stainless steel disks treated with the silver sulfadiazine. The lowest bacterial values were found in the other control group in which silver sulfadiazine was used directly on the inoculated agar surface. The Biobrane sample group exhibited a high bacterial value after 6 hours with only a small difference with respect to the stainless-steel disks group, while the polyurethane layer according to the invention exhibited a low bacterial value with virtually no difference compared with the control group involving direct use of silver sulfadiazine.

The bacterial value in the agar under Biobrane disks decreased 24 hours after the silver sulfadiazine was used, but remained appreciably higher than for the polyurethane group according to the invention and also the control group, which indicates that silver sulfadiazine used on Biobrane slowly penetrates the agar and does not achieve the full antimicrobial effect as in the two lastnamed other groups.

EXAMPLE IV

In this example, the adhesion properties of the upper layer, various types of lower layer and the artificial skin according to the invention itself to the bed of the wound are investigated and compared with that of a skin transplant (autograft) and the commercial product "Biobrane".

Figure 6:
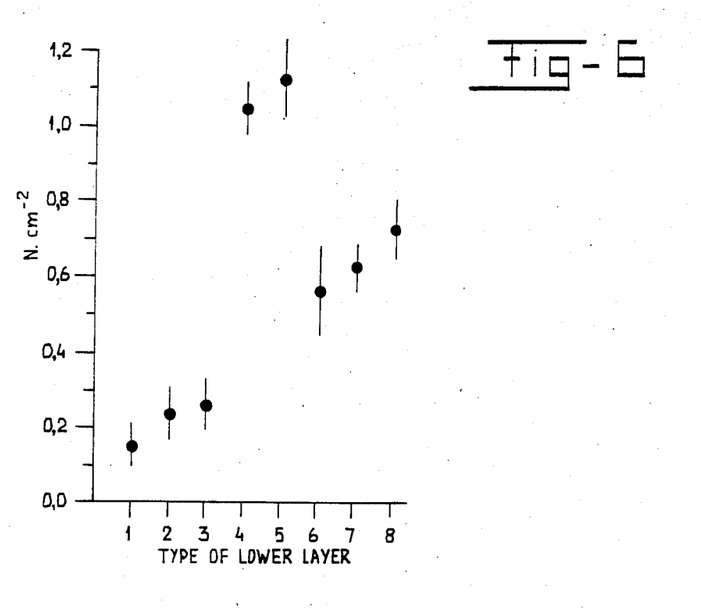
FIG. 6: Graphical representation of the tensiometrical results determined 5 hours after applying the artificial covering of the structural types 1-6, "Biobrane" (structural type 7) and an autograft (structural type 8) to the induced wound bed (2 cm×8 cm) for nonheparinized guinea pigs.
Figure 7:
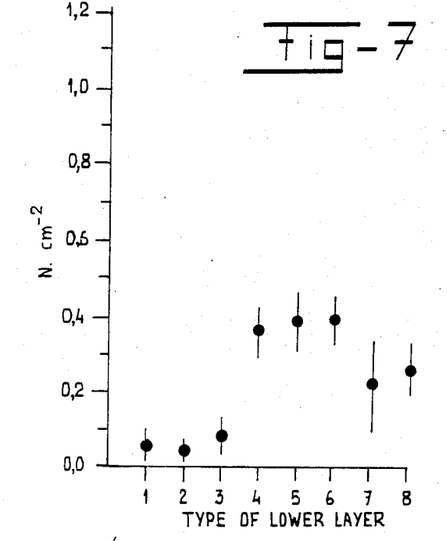
FIG. 7: Graphical representation of the tensiometric results determined 5 hours after applying the artificial covering of the structural types 1-6, "Biobrane" (structural type 7) and an autograft (structural type 8) to the induced wound bed (2 cm×8 cm) of heparinized guinea pigs (intravenous injection of 400 units of heparin and spraying of the bed of the wound (2 cm×8 cm) with 5 ml of a physiological saline solution containing 2,000 units of heparin before the application of the artificial covering).

Manufacture of the lower layer types 1, $\frac{2}{3}$ and 4 and also of the artificial skin according to the invention (see FIGS. 6+7)

(A) Manufacture of a smooth polyurethane layer (type 1)

A solution of the commercial product "Biomer" in N,N-dimethylacetamide (11.5 g/100 ml) was prepared. This solution was applied to a glass plate having dimensions of 40 cm×40 cm, which glass plate had been rinsed beforehand with ethanol and dried in air. The Biomer solution was spread out over the glass plate and adjusted to a thickness of 300 μm with an adjustable skimming device. Then the solvent N,N-dimethylacetamide was removed by evaporation.

(B) Manufacture of a polyurethane layer containing macropores (type $\frac{2}{3}$)

A solution of the commercial product "Biomer" in N,N-dimethylacetamide (3 g/100 ml) was prepared. This solution was applied to a glass plate having dimensions of 40 cm×40 cm, which glass plate had been rinsed beforehand with ethanol and dried in air. The Biomer solution was spread out over the glass plate and adjusted to a thickness of 350 μm with an adjustable skimming device. Then the layer obtained was immersed in ethanol (100%) for 10 minutes, which resulted in a coagulation of the layer. A layer was obtained which had macropores having a diameter of 50 to 100 μm.

(C) Manufacture of lower layer type 4

This lower layer was manufactured in accordance with the manner described in Example 1.

The initial in vivo wound adhesion determined 5 hours after applying the artificial covering or skin transplant to the bed of the wound (2 cm×8 cm).

Tensiometry results in group (1) (nonheparinized guinea pigs; n=24) indicated that a smooth polyurethane layer (type 1) has only initial adhesion values. The provision therein of macropores (types 2 and 3) increased the initial adhesion to some extent. The prototype 4 which combined within it the macropores, a fibrillated sponge structure containing globular precipitation and micropores exhibited the highest initial adhesion value for the lower layer structure, being 1.03N/cm$^2$. This lower layer with optimum adhesion was combined with the microporous upper layer (type 6). This combination resulted in the most adhesive version of the artificial skin according to the invention which had an initial adhesion value of 1.13N/cm$^2$ (see type 5 in FIG. 6). In FIG. 6, Biobrane is indicated as type 7 and the autograft as type 8.

The tensiometry results determined in a corresponding manner in group (2) (guinea pigs heparinized intravenously with 400 units of heparin, the bed of the wound being sprayed with 5 ml of a physiological saline solution containing 2,000 units of heparin before applying the artificial covering; n=24) exhibited a dramatic decrease in the initial adhesion value with respect to group (1), which is evident from FIG. 7.

The in vivo wound adhesion during the wound healing process (2 cm×8 cm; n=21)

Figure 8:
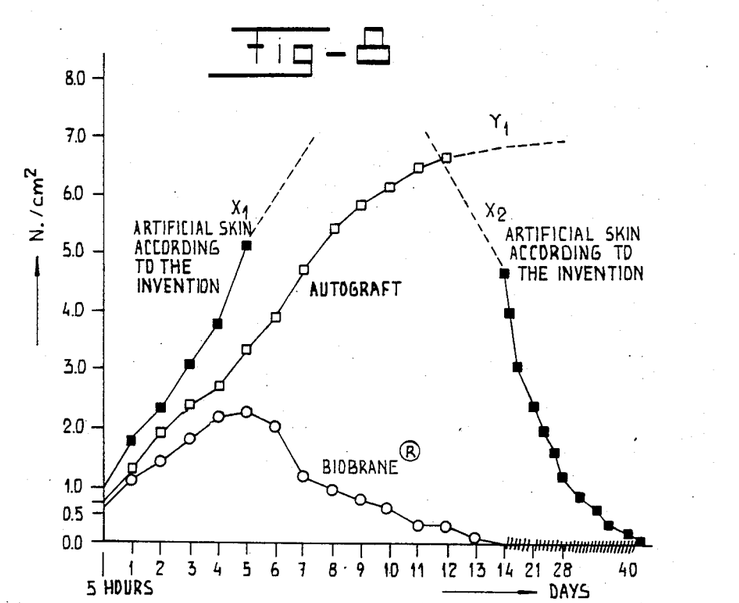
FIG. 8: Graphical representation of the tensiometric results of the artificial skin according to the invention, an autograft and Biobrane during the course of the healing process.

The mean tensiometric values for a number of materials investigated for the in vivo wound adhesion during the wound healing process are shown in FIG. 8. The artificial skin according to the invention exhibited the highest initial adhesion value (1.13N/cm$^2$) compared with the autograft (0.74N/cm$^2$) and Biobrane (0.61N/cm$^2$). After 5 days, the artificial skin according to the invention became so strongly bonded to the bed of the wound that an attempt to detach the prosthesis resulted in the membrane tearing away from the bed of the wound (see point X$_1$ in FIG. 8). The autografts exhibited increasing adhesion values until the measurements corresponded in principle to the tearing away of normal skin tissue. Biobrane exhibited an initial increase in the adhesion but after the fifth day a decrease in the adhesion value, corresponding to the progressive development of blisters under the Biobrane.

EXAMPLE V

In vivo investigation of the combined upper layer and lower layer according to the invention manufactured according to Example I (n=8)

The same functions were determined for the combined upper and lower layers according to the invention as for the microporous upper layer. The above tests were carried out using guinea pigs having a "full-thickness" skin lesion. In the tests, use was made of groups each containing 8 specimens (artificial skin according to the invention, Biobrane and "full-thickness" autograft) using strips of artificial skin measuring 2×8 cm.

(1) Evaporimetry

Figure 9:
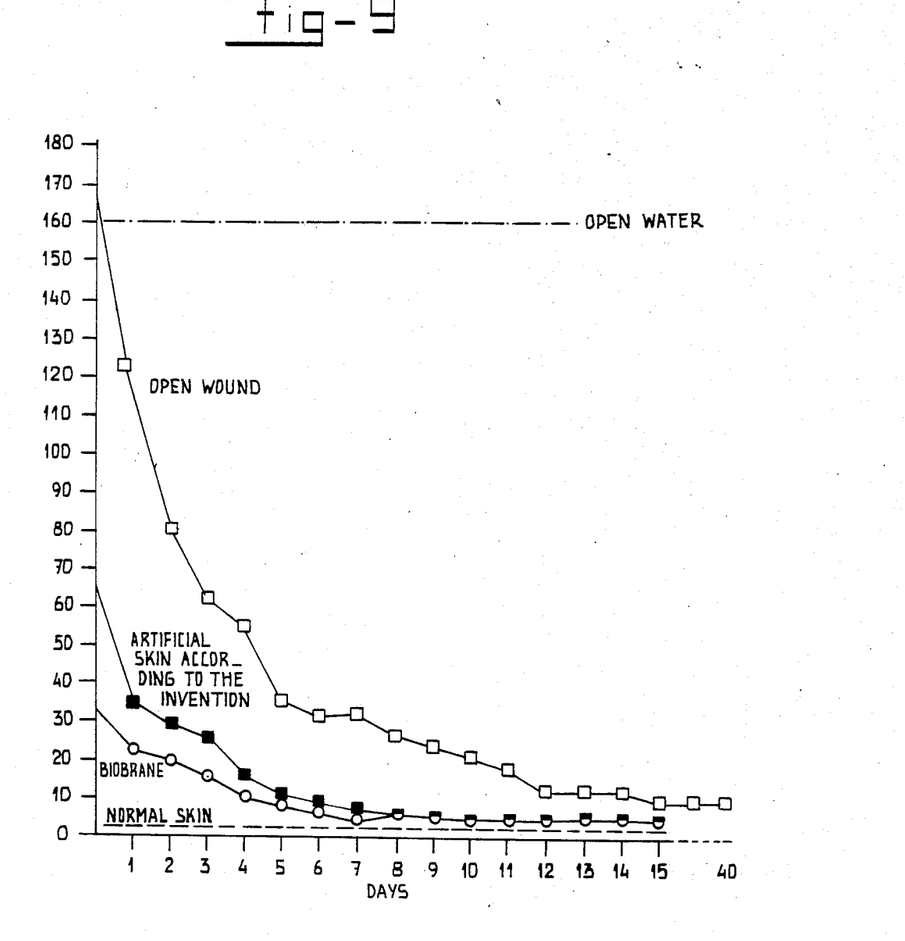
FIG. 9: Graphical representation of the evaporimetric in vivo values of an open wound, the artificial skin according to the invention, Biobrane and normal skin during the course of the healing process.

A wound covering using an artificial skin according to the invention and Biobrane respectively resulted in a water vapour loss from the wound surface of 40 and 18% respectively (see FIG. 9). One day after use, the water vapour loss (EWL) for both materials decreased further to 21% for the artificial skin according to the invention and 15% for Biobrane. During the subsequent days, the EWL value of both materials decreased continuously. It was possible to carry out the measurements carried out with Biobrane in the second week only on two samples, which samples remained in situ until the fifteenth day. The evaporimeter measuring point was held above the bonded regions of the Biobrane and not above the liquid-filled blisters.

(2) Wound drainage

Both the comparison material Biobrane and the artificial skin according to the invention continued to adhere to the bed of the wound for the first three days. On the third day, however, a development of small blisters was observed beneath the Biobrane materials. This process ultimately resulted in the formation of pus-containing blisters during the first week, which resulted in a shedding of the Biobrane material from the surface of the wound. 6 guinea pigs lost the Biobrane material before the end of the first week. The Biobrane material remained in situ until the twelfth and the fifteenth day for only two specimens. On the other hand, the artificial skin material according to the invention adhered without any sign of blister formation for the total residence of 42 days on the wound.

(3) Controlled wound infection and local antibiotic therapy

Figure 10:
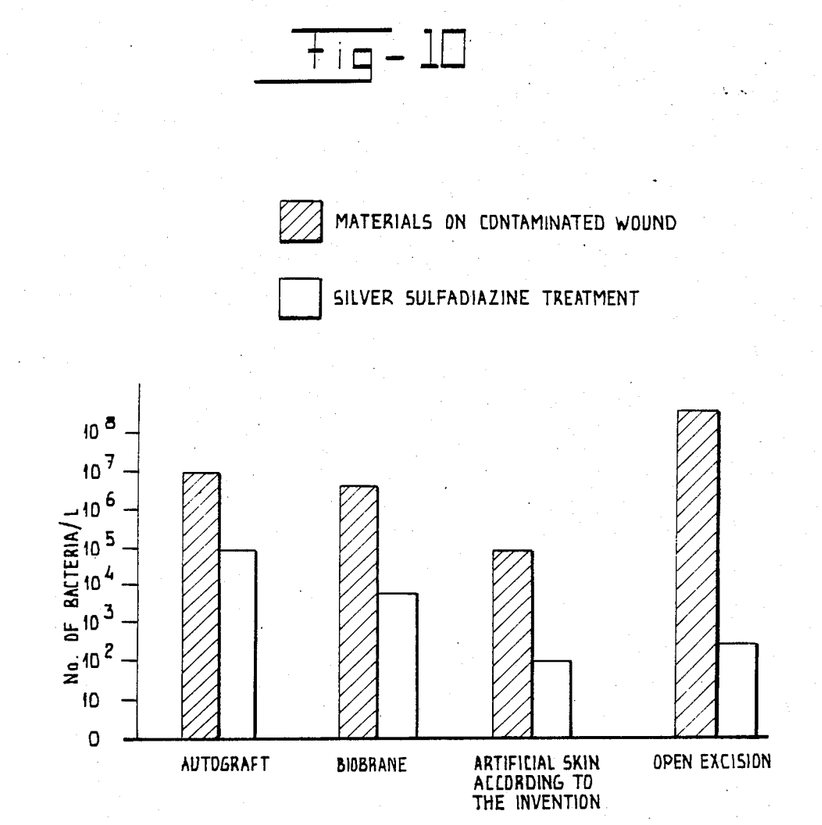
FIG. 10: Graphical representation of the in vivo silversulfadiazine penetration in the case of an autograft, Biobrane, the artificial skin according to the invention and an open excision which have been deliberately inoculated with *Pseudomonas aeruginosa* bacteria.

The abovementioned wounds were deliberately inoculated with a bacterial suspension of rapidly dividing Ps. aeruginosa bacteria. The lowest bacterial value was found in the case of the artificial skin according to the invention (see FIG. 10), followed by Biobrane. The bactericidal effect of the silver sulfadiazine treatment was clearest for both the group having the artificial skin according to the invention and the open-wound control group. An incomplete penetration effect was observed in the case of Biobrane and autograft.

EXAMPLE VI

Comparison of an artificial skin according to the invention with a biodegradable lower layer manufactured according to Example II (n=7) and nonbiodegradable lower layer manufactured according to Example I (n=7)

In this test, both types of artificial skin according to the invention continued to adhere to the bed of the wound for the entire wound healing process (7 weeks). No liquid accumulation or infection occurred during the period of use. As a result of this, renewal or replacement of the artificial skin was unnecessary. The wound healing process appeared macroscopically to be identical. The proliferating granulation tissue was clearly observable through the transparent upper layer and appeared as a rosy layer beneath the artificial skin. The epidermis regenerated starting from the corners of the wound with the separation of a crust-like layer which appeared to contain artificial skin material. The detached artificial skin was regularly tidied up from the corners of the wound. A morphometric quantification of the wound contraction values exhibited no important differences between nondegradable and biodegradable artificial skins. Both exhibited a total reduction in wound surface area of 52%, which is appreciably less than the reduction of 88% of the untreated control group which also had a full-thickness skin lesion. The wounds treated with artificial skin according to the invention yielded a trapezoidal scar tissue after 7 weeks of implantation, which indicates that epithelization of the remaining surface area of the open wound had occurred. In the untreated control group this healing process was accomplished after 6 weeks by the crust falling off. The healed wound appeared to contain irregular longitudinal scar tissue with a narrow region of epithelization.

The histology of the untreated open wound control group indicated that the epidermis grew over the granulation tissue under the wound crust. Both the biodegradable and nonbiodegradable lower layer of the artificial skin according to the invention exhibited a rapid growing-in of granulation tissue starting from the bed of the wound, with the result that the artificial skin became a part of the new neodermis. In particular, the important differences were demonstrated in the participation of the artificial skin in the neodermis formation. In the biodegradable artificial skin, the polymer fibrilla of the lower layer were surrounded by giant cells and decreased considerably in thickness in the 4th to the 6th week, while the nondegradable lower layer of the artificial skin remained unattacked by the giant cells and retained the original structure during the entire healing process.

The process of epidermal wound healing also exhibited a large difference between the two types of artificial skin indicated above. In the biodegradable lower layer, epidermal shoots penetrated the interface between the nonbiodegradable upper layer and the biodegradable lower layer from the wound edges and thus grew over the granulation tissue which had grown into the lower layer. This process of epidermal invasion led to the detachment of the protective upper layer and resulted in a healed wound which was covered with new epidermis and a fibrous "neodermis" containing polymer particles. The amount of biodegradable polymer particles decreased during the healing period.

In the nonbiodegradable lower layer of the artificial skin according to the invention the ingrowing epidermis was situated in the interface between the lower layer of the artificial skin and the granulation tissue which covered the wound surface. This led to loss of the complete artificial skin (upper and lower layers) and resulted in a healed wound surface which was covered with epidermis. This healed wound did not contain any polymer particles.

In the case of both the biodegradable and the nonbiodegradable artificial skin, the healed epidermis was firmly stuck to the lower layer by means of epidermal "pseudopodia".

CAPTIONS

We claim:

1. Artificial skin which transmits wound moisture, comprising
    (a) an upper layer of an elastomer having a thickness of 0.01–0.2 mm which is provided with pores having a diameter not exceeding 0.7 μm and a pore density of 1–75% of the surface, and
    (b) a lower layer of an elastomer having a thickness of 0.05–1 mm which is provided with macropores having a diameter of 50–200 μm interspersed throughout the thickness of said lower layer with micropores having a diameter of 0.1–0.25 μm.

2. Artificial skin according to claim 1, characterized in that the upper layer is provided with pores having a diameter of 0.2–0.44 μm.

3. Artificial skin according to claim 1, characterized in that the thickness of the upper layer is 0.02–0.1 mm.

4. Artificial skin according to claim 1, characterized in that the pore density of the upper layer is 25–40% of the surface area.

5. Artificial skin according to claim 1, characterized in that the lower layer is manufactured from a nonbiodegradable elastomer.

6. Artificial skin according to claim 1, characterized in that the thickness of the lower layer is 0.1–0.7 mm.

7. Artificial skin according to claim 1, characterized in that the ratio of vacant volume to total volume for the lower layer is in the range of 0.5–0.95.

8. Artificial skin according to claim 1, characterized in that a polyurethane having elastomeric properties is used as elastomer.

9. Artificial skin according to claim 8, characterized in that, as elastic polyurethane, use is made of a polyether urethane or a polyester urethane which is based on the elements chosen from the group comprising polytetramethylene adipate, polyethylene glycol adipate, polytetramethylene oxide, polydiethylene glycol adipate, 3,4'- and 4,4'-diphenylmethane diisocyanate, toluene diisocyanate and hexamethylene diisocyanate.

10. Artificial skin according to claim 1, wherein the ratio of vacant volume to total volume for the lower layer is in the range of 0.7–0.9.

* * * * *